US010155371B2

United States Patent
Nally et al.

(10) Patent No.: US 10,155,371 B2
(45) Date of Patent: Dec. 18, 2018

(54) DETERMINING AN AUTOMATIC BONDING SEQUENCE FOR OPTICAL BONDING

(71) Applicant: PRECISION VALVE & AUTOMATION, INC., Cohoes, NY (US)

(72) Inventors: Andrew John Nally, Ballston Spa, NY (US); Alexander M. Giordano, Ballston Lake, NY (US); Edward F. Carey, Ballston Spa, NY (US); Jonathan Neal Urquhart, Saratoga Springs, NY (US)

(73) Assignee: PRECISION VALVE & AUTOMATION, INC., Cohoes, NY (US)

( * ) Notice: Subject to any disclaimer, the term of this patent is extended or adjusted under 35 U.S.C. 154(b) by 38 days.

(21) Appl. No.: 15/585,684

(22) Filed: May 3, 2017

(65) Prior Publication Data

US 2017/0320310 A1    Nov. 9, 2017

Related U.S. Application Data

(60) Provisional application No. 62/331,257, filed on May 3, 2016.

(51) Int. Cl.
*B23B 41/00* (2006.01)
*B32B 41/00* (2006.01)
(Continued)

(52) U.S. Cl.
CPC ............ *B32B 41/00* (2013.01); *B29C 65/48* (2013.01); *B29C 66/90* (2013.01); *B29D 11/00* (2013.01);
(Continued)

(58) Field of Classification Search
None
See application file for complete search history.

(56) References Cited

U.S. PATENT DOCUMENTS 7,364,633 B2    4/2008    Lim et al.
7,819,159 B2    10/2010   Ito et al.
(Continued)

FOREIGN PATENT DOCUMENTS

| KR | 100878466 B1 | 1/2009 |
| KR | 20160009556 A | 2/2014 |
| KR | 20160022297 A | 6/2014 |

OTHER PUBLICATIONS

International Search Report and Written Opinion for PCT Application No. PCT/US2017/030774, dated Jul. 13, 2017.
(Continued)

*Primary Examiner* — Ryan A Jarrett
(74) *Attorney, Agent, or Firm* — Schmeiser, Olsen & Watts, LLP (57) ABSTRACT

An automated bonding sequence system and method for customizing a bonding sequence is provided. The method includes the steps of detecting that a first substrate is in close proximity with the a second substrate, during an optical bonding operation, wherein at least the first substrate includes an amount of adhesive for optically bonding to the second substrate, stopping an automated process of optically bonding of the optical bonding operation, in response to the detecting, recording operator feedback control signals, the operator feedback control signals being received from a controller being operated by an operator to contact the first substrate and the second substrate, analyzing the operator feedback control signals to determine a bonding sequence for automatically optically bonding the first substrate and the
(Continued)

second substrate, and resuming, by the processor, the automated process of the optical bonding operation.

20 Claims, 9 Drawing Sheets

(51) Int. Cl.
| | |
|---|---|
| *G05B 19/409* | (2006.01) |
| *B29C 65/48* | (2006.01) |
| *B29C 65/00* | (2006.01) |
| *H04N 7/18* | (2006.01) |
| *B29D 11/00* | (2006.01) |
| *B32B 17/10* | (2006.01) |
| *B32B 37/00* | (2006.01) |
| *B32B 37/12* | (2006.01) |
| *B29L 11/00* | (2006.01) |
| *G06T 7/00* | (2017.01) |

(52) U.S. Cl.
CPC ...... *B32B 17/10807* (2013.01); *B32B 37/003* (2013.01); *G05B 19/409* (2013.01); *H04N 7/183* (2013.01); *B29L 2011/00* (2013.01); *B32B 37/12* (2013.01); *B32B 37/1284* (2013.01); *B32B 2037/1253* (2013.01); *B32B 2041/04* (2013.01); *B32B 2041/06* (2013.01); *B32B 2307/412* (2013.01); *B32B 2309/70* (2013.01); *B32B 2457/20* (2013.01); *G05B 2219/49032* (2013.01); *G06T 7/0008* (2013.01); *G06T 2207/10016* (2013.01)

(56) References Cited

U.S. PATENT DOCUMENTS

| | | |
|---|---|---|
| 8,764,930 B2 | 7/2014 | Shabata et al. |
| 10,007,369 B1* | 6/2018 | Noh ................... G06F 3/0412 |
| 2010/0197187 A1 | 8/2010 | Naraba et al. |
| 2011/0292623 A1 | 1/2011 | Stanley |
| 2012/0234459 A1 | 9/2012 | Nally et al. |
| 2013/0112650 A1* | 5/2013 | Karam ................ B32B 37/06 216/13 |
| 2013/0344302 A1* | 12/2013 | Helie ................ B23K 26/0057 428/195.1 |
| 2014/0182780 A1 | 7/2014 | Jung et al. |
| 2015/0027618 A1 | 1/2015 | Orisni |
| 2015/0357253 A1 | 12/2015 | Babiarz et al. |
| 2016/0159061 A1* | 6/2016 | Nally ................ B32B 17/10807 156/64 |

OTHER PUBLICATIONS

International Search Report and Written Opinion for PCT Application No. PCT/US2017/030791, dated Aug. 1, 2017.

* cited by examiner

DETERMINING AN AUTOMATIC BONDING SEQUENCE FOR OPTICAL BONDING

CROSS-REFERENCE TO RELATED APPLICATIONS

This application claims priority to and the benefit of U.S. Provisional Application No. 62/331,257, filed May 3, 2016, and entitled "Optical Bonding Machine," the entire contents of which hereby incorporated by reference.

TECHNICAL FIELD

The following relates to an automatic bonding sequence learning system, and more specifically to embodiments of determining a bonding sequence for optically bonding two substrates.

BACKGROUND

Optical bonding involves bonding two substrates together using an optically clear adhesive. An ideal bond does not include the presence of air pockets between the substrates. To prevent or hinder a formation of air pockets, the substrates must be bonded together to create a capillary effect of the adhesive sandwiched between the substrates.

SUMMARY

A first aspect relates to a method for customizing an automated bonding sequence, the method comprising: detecting, by a processor of a computing system, that a first substrate is in close proximity with the a second substrate, during an optical bonding operation, wherein at least the first substrate includes an amount of adhesive for optically bonding to the second substrate, stopping, by the processor, an automated process of optically bonding of the optical bonding operation, in response to the detecting, recording, by the processor, operator feedback control signals, the operator feedback control signals being received from a controller being operated by an operator to contact the first substrate and the second substrate, analyzing, by the processor, the operator feedback control signals to determine a bonding sequence for automatically optically bonding the first substrate and the second substrate, and resuming, by the processor, the automated process of the optical bonding operation.

A second aspect relates to a computer system, comprising: a processor, a memory device coupled to the processor, and a computer readable storage device coupled to the processor, wherein the storage device contains program code executable by the processor via the memory device to implement a method customizing an automated bonding sequence, the method comprising: detecting, by a processor of a computing system, that a first substrate is in close proximity with the a second substrate, during an optical bonding operation, wherein at least the first substrate includes an amount of adhesive for optically bonding to the second substrate, stopping, by the processor, an automated process of optically bonding of the optical bonding operation, in response to the detecting, recording, by the processor, operator feedback control signals, the operator feedback control signals being received from a controller being operated by an operator to contact the first substrate and the second substrate, analyzing, by the processor, the operator feedback control signals to determine a bonding sequence for automatically optically bonding the first substrate and the second substrate, and resuming, by the processor, the automated process of the optical bonding operation.

A third aspect relates to a computer program product, comprising a computer readable hardware storage device storing a computer readable program code, the computer readable program code comprising an algorithm that when executed by a computer processor of a computing system implements a method customizing an automated bonding sequence, the method comprising: detecting, by a processor of a computing system, that a first substrate is in close proximity with the a second substrate, during an optical bonding operation, wherein at least the first substrate includes an amount of adhesive for optically bonding to the second substrate, stopping, by the processor, an automated process of optically bonding of the optical bonding operation, in response to the detecting, recording, by the processor, operator feedback control signals, the operator feedback control signals being received from a controller being operated by an operator to contact the first substrate and the second substrate, analyzing, by the processor, the operator feedback control signals to determine a bonding sequence for automatically optically bonding the first substrate and the second substrate, and resuming, by the processor, the automated process of the optical bonding operation.

DETAILED DESCRIPTION

Figure 1:
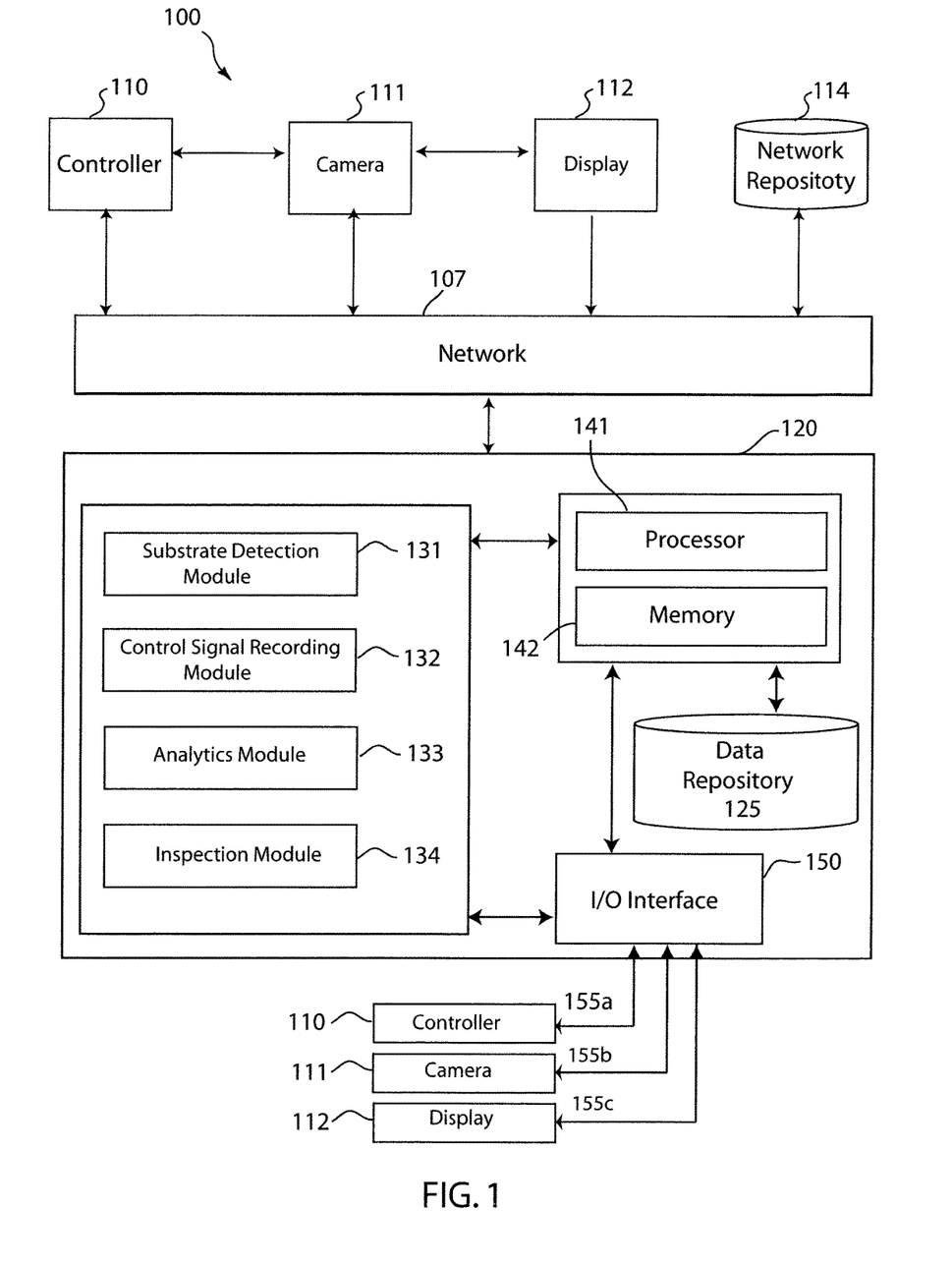
FIG. 1 depicts a block diagram of automatic bonding sequence learning system, in accordance with embodiments of the present invention.

Referring to the drawings, FIG. 1 depicts a block diagram of automatic bonding sequence learning system 100, in accordance with embodiments of the present invention. Embodiments of the automatic bonding sequence learning system 100 may determine a customized bonding sequence for various sized substrates and various optically clear adhesives during an automated optical bonding process. The automatic bonding sequence learning system 100 may record control signals from an operator using a controller to bring the substrates together during an initial bonding sequence, and then analyze the signals to determine an automated bonding sequence to be used in subsequent applications/processes. For instance, for a new or initial automated optical bonding process, an operator may manually control the actual bonding process step (e.g. controllably lowering the top substrate onto the bottom substrate) of the automated process to ensure a proper wavefront progression of the adhesive and end result (e.g. no air pockets, full visible area wet out, desired bond thickness), given the size of the substrates and adhesive used for a particular application. Thus, an optical bonding machine provided to an end user may be flexible to perform an automated optical bonding process for more than one size substrate(s) or application, wherein the appropriate bonding sequence may be automatically determined based on an initial (e.g. a single unit being bonded) run.

Embodiments of the automatic bonding sequence learning system 100 may include a computing system 120. Embodiments of the computing system 120 may be an onboard computing system of a machine, such as an optical bonding machine. In other embodiments, the computing system 120 may be a server or remote computing system communicatively coupled to an onboard computing system of the machine, wherein the computing system 120 services requests and performs the functions of the automatic bonding sequence learning system 100.

Embodiment of automatic bonding sequence learning system 100 may comprise a controller 110, a camera 111, and a display 112 communicatively coupled to a computing system 120 via an I/O interface 150 and/or over a network 107. For instance, the controller 110, the camera 111, and the display 112 may be connected via an I/O interface 150 to computer system 120. The number of controllers 110, cameras 111, and displays 112 connecting to computer system 120 via data bus lines 155a, 155b (referred to collectively as "data bus lines 155) and/or over network 107 may vary from embodiment to embodiment.

As shown in FIG. 1, the controller 110 may transmit control signals/data (e.g. "machine data" and/or "bonding sequence data") by connecting to computing system 120 via the data bus lines 155 to an I/O interface 150. The camera 111 may transmit image and/or video data ("bonding sequence data) by connecting to computing system 120 via the data bus lines 155 to an I/O interface 150. The display 112 may receive display data to display the bonding sequence data transmitted to the computing system 120 by the camera 111. An I/O interface 150 may refer to any communication process performed between the computer system 120 and the environment outside of the computer system 120, for example, the controller 110, the camera 111, and the display 111. Input to the computing system 120 may refer to the signals or instructions sent to the computing system 120, for example, the controller signals transmitted by the controller 110, while output may refer to the signals sent out from the computer system 120 to the display 110, or other components of the optical bonding machine (e.g. end effector, LED array, robotic placement head which picks and places the top substrate).

Alternatively, the controller 110, camera 111, and display 112 may transmit or receive data by connecting to computing system 120 over the network 107. A network 107 may refer to a group of two or more computer systems linked together. Network 107 may be any type of computer network known by individuals skilled in the art. Examples of computer networks 107 may include a LAN, WAN, campus area networks (CAN), home area networks (HAN), metropolitan area networks (MAN), an enterprise network, cloud computing network (either physical or virtual) e.g. the Internet, a cellular communication network such as GSM or CDMA network or a mobile communications data network. The architecture of the computer network 107 may be a peer-to-peer network in some embodiments, wherein in other embodiments, the network 107 may be organized as a client/server architecture. In an exemplary embodiment, network 107 may be an Ethernet network of a machine, such as an optical bonding machine.

In some embodiments, the network 107 may further comprise, in addition to the computer system 120, controller 110, camera 111, and display 112, a connection to one or more network accessible knowledge bases containing information of one or more users, network repositories 114 or other systems connected to the network 107 that may be considered nodes of the network 107. In some embodiments, where the computing system 120 or network repositories 114 allocate resources to be used by the other nodes of the network 107, the computer system 120 and network repository 114 may be referred to as servers.

The network repository 114 may be a data collection area on the network 107 which may back up and save all the data transmitted back and forth between the nodes of the network 107. For example, the network repository 114 may be a data center saving and cataloging machine data and/or bonding sequence data sent by one or more of the controller 110, camera 111 or received by display 112, to generate both historical and predictive reports regarding a particular bonding sequence for a given application or project. In some embodiments, a data collection center housing the network repository 114 may include an analytic module capable of analyzing each piece of data being stored by the network repository 114. Further, the computer system 120 may be integrated with or as a part of the data collection center housing the network repository 114. In some alternative embodiments, the network repository 114 may be a local repository (not shown) that is connected to the computer system 120.

With continued reference to FIG. 1, embodiments of the computing system 120 may receive the machine data and/or bonding sequence data from the controller 110 or camera 111 which may be positioned within an interior of the optical bonding machine, on an exterior surface of the machine, remotely, in an environment shared by an operator, or otherwise disposed in a location that can result in obtaining machine data and bonding sequence data. In an exemplary embodiment, the controller 110 may be removably attached to the machine, connected to the computing system 120 via cord, so that an operator may operate the controller 110 with a view of the display 112, which is coupled to the computing system 120. The controller 110 may also be a remote controller connecting to the computing system 120 via network 107, or other wireless network. The camera 111 may be positioned underneath the bottom substrate, while the display 112 may be attached to a frame of a machine.

Figure 2A:
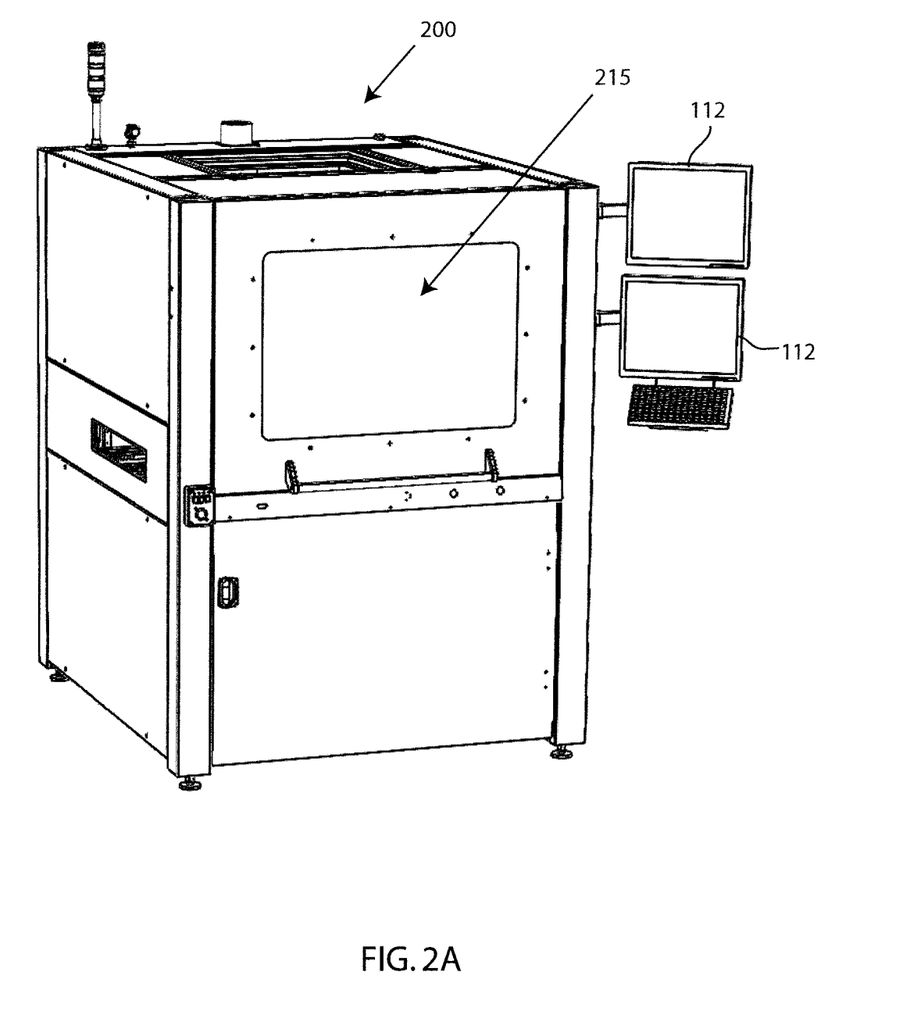
FIG. 2A depicts an optical bonding machine, in accordance with embodiments of the present invention.
Figure 2B:
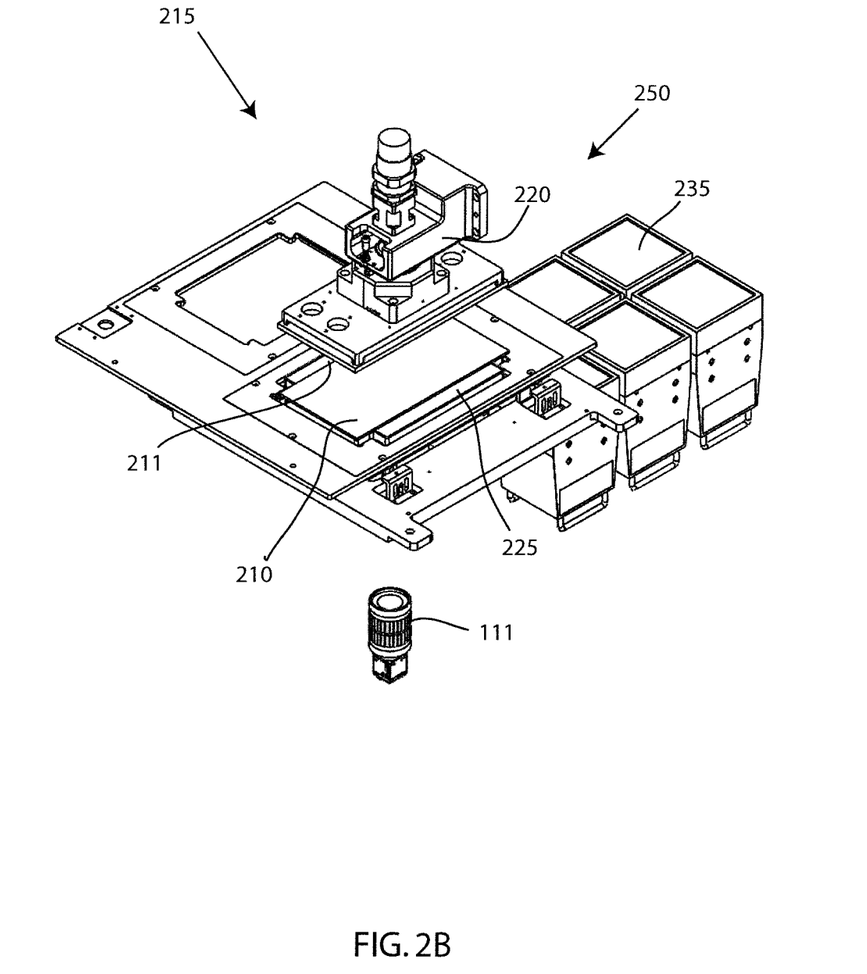
FIG. 2B depicts a schematic view of an optical bonding assembly located within an interior region of the optical bonding machine of FIG. 2A, in accordance with embodiments of the present invention.
Figure 2C:
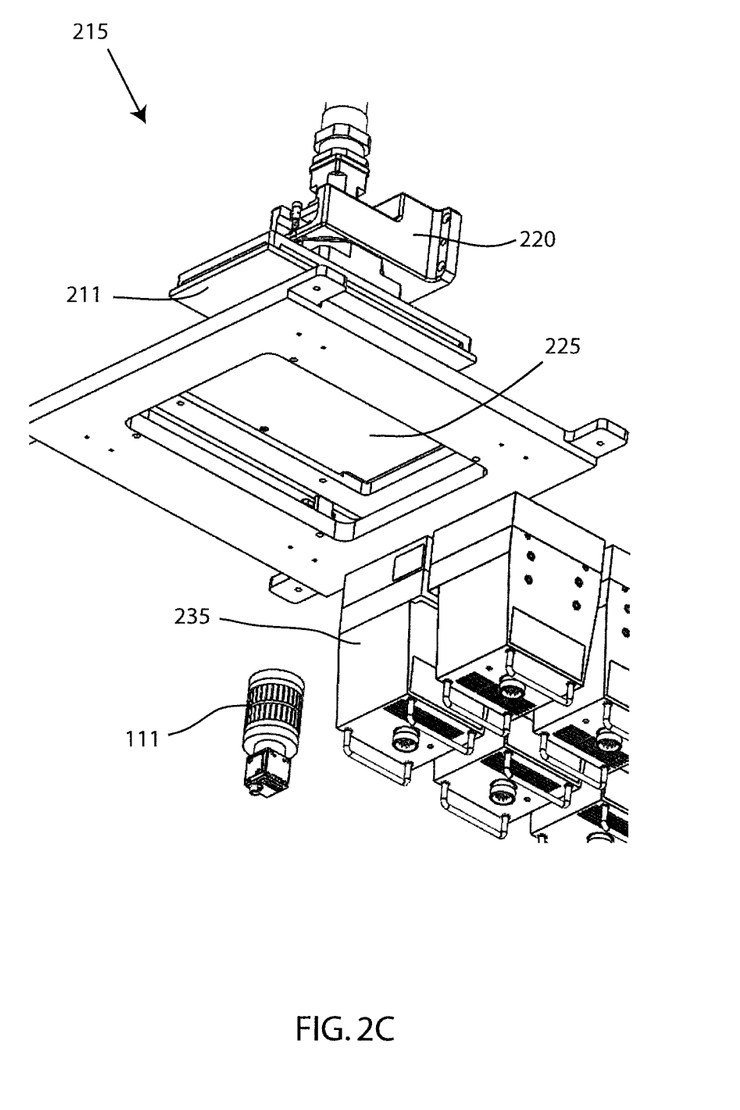
FIG. 2C depicts a schematic view from underneath the optical bonding assembly of FIG. 2B, in accordance with embodiments of the present invention.

FIGS. 2A-2B depict embodiments of an optical bonding machine, which may be operated and/or controlled by computing system 120. FIG. 2A depicts an optical bonding machine 200, in accordance with embodiments of the present invention. Embodiments of the optical bonding machine 200 may include an interior region 215, wherein various components, such as the robotic placement head that picks and places one of the substrates, datum, camera 111, end effector, etc., reside for carrying out an optical bonding process. One or more displays 112 may be attached to a frame of the machine 200, for viewing image or video data captured by the camera 111 located underneath a datum that supports the bottom substrate. FIG. 2B depicts a schematic view of an optical bonding assembly 250 located within the interior region 215 of the optical bonding machine 200 of FIG. 2A, in accordance with embodiments of the present invention. Embodiments of the optical bonding assembly 250 may represent only a number of components associated with the optical bonding machine 200, wherein the optical bonding machine 200 may include several other components, including an end effector, gantry robot, X, Y, Z and theta, servo actuators, and the like. Embodiments of the optical bonding assembly 250 may include a datum 225, which may support a first substrate 210, such as a bottom substrate. The datum 225 may be transparent, so that the bonding between the first substrate 210 and a second substrate 210 may be visible from the camera 110 disposed underneath the datum 225. The first substrate 210 and the second substrate 211 may be an optically clear substrate, such as a piece of glass for use as a display or cover glass for a computing device or other smart surface (e.g. smart phone, tablet, vehicle touch screen, etc.). One or both of the first substrate 210 and the second substrate 211 may be a capacitive screen. Further, embodiments of the optical bonding assembly 150 may include a robotic placement head 220, for picking and placing the second substrate 211 into contact with the first substrate 210. The robotic placement head 220 may have movement along the X axis, Y axis, and Z axis, as well as rotational and tilting capabilities, for example, through ball screw slides and gantry robot configuration. The robotic placement head 220 may move in a manner to optically bond the substrates 210, 211, while the camera 111 captures a progression of the adhesive between the substrates 210, 211 as the substrates 210, 211 are bonded together. The video or image data may be transmitted to the computing system 120 so the computing system 120 can display the footage on display 112, during the bonding process. FIG. 2C depicts a schematic view from underneath the optical bonding assembly 250 of FIG. 2B, in accordance with embodiments of the present invention. The camera 111 may be positioned underneath a transparent datum 225 to capture the flow of the adhesives between the substrates 210, 211. Further, embodiments of the optical bond assembly 250 may include a UV source, such as LED array 235. The UV source 235 may be actuated by the computing system 120 to move in a position directly underneath the datum 225 to cure the adhesive, after the substrates 210, 211 have bonded and potentially an inspection for air pockets or other defects has taken place.

Referring back to FIG. 1, embodiments of the computing system 120 may include a substrate detection module 131, a control signal recording module 132, an analytics module 133, and an inspection module 135. A "module" may refer to a hardware based module, software based module or a module may be a combination of hardware and software. Embodiments of hardware based modules may include self-contained components such as chipsets, specialized circuitry and one or more memory devices, while a software-based module may be part of a program code or linked to the program code containing specific programmed instructions, which may be loaded in the memory device of the computer system 120. A module (whether hardware, software, or a combination thereof) may be designed to implement or execute one or more particular functions or routines.

Figure 3:
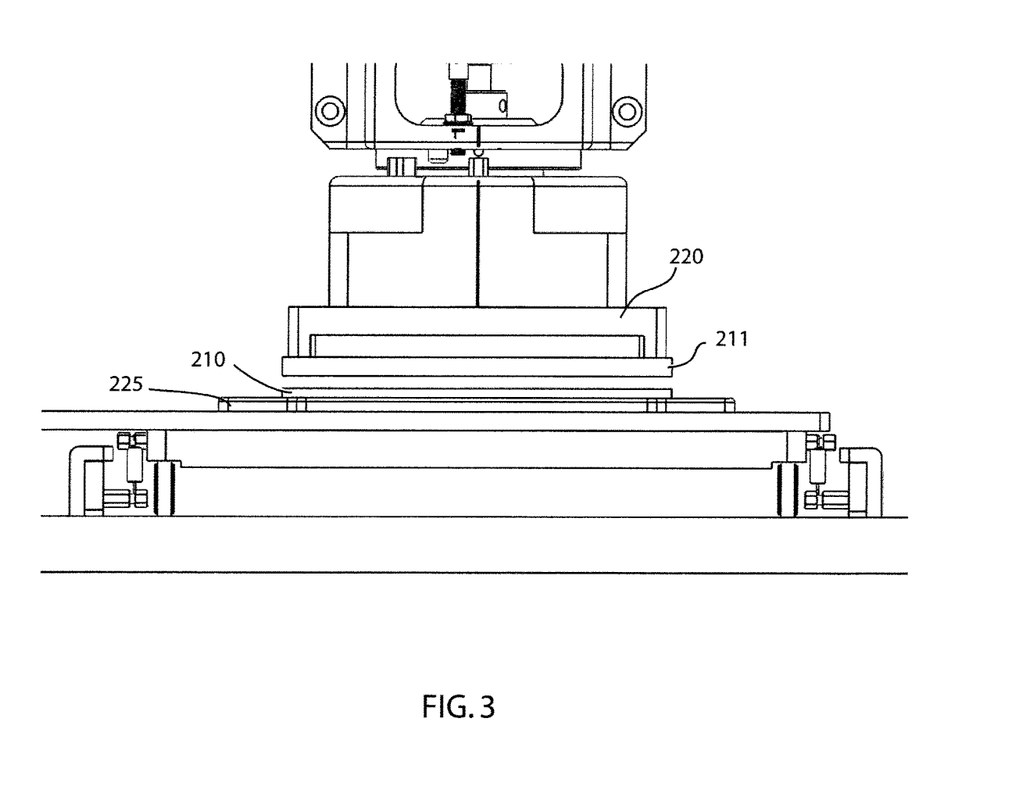
FIG. 3 depicts a close proximity between the first substrate and the second substrate, during an optical bonding process, in accordance with embodiments of the present invention.

Embodiments of the substrate detection module 131 may include one or more components of hardware and/or software program code for detecting that a first substrate 210 is in close proximity with the a second substrate 211 (or vice versa), during an optical bonding operation. FIG. 3 depicts a close proximity between the first substrate 210 and the second substrate 211, during an optical bonding process, in accordance with embodiments of the present invention. Close proximity may mean that a small gap exists between the first substrate 210 and the second substrate 211, wherein an adhesive material dispensed on the first substrate 210 has yet to come into contact with an adhesive material on the second substrate 211 (e.g. a dot of adhesive on the underside of the second substrate). The gap between the first substrate 210 and the second substrate 211 may be smaller or significantly smaller than the gap between the substrates 210, 211 shown in FIGS. 2A-2C. The gap when in close proximity may be several millimeters or larger. Embodiments of the substrate detection module 131 may detect when the robotic placement head 220 advanced close enough to the datum 225, to determine that a close proximity exists. In an exemplary embodiment, the movement of the robotic placement head 220 is pre-programmed to automatically reach a close proximity, and in response to arriving at a location of close proximity, the substrate detection module 131 may stop the movement of the robotic placement head 220. In another exemplary embodiment, the substrate detection module 131 may confirm that substrates 210, 211 are in close proximity by scanning the area surrounding the first substrate 210, and transmitting a signal to the computing system 120 to cease movement of the robotic placement head 220 in response to a detection of a lead edge of the second substrate 210. In yet another exemplary embodiment, close proximity is detected using a touch probe early on in the process to measure the thickness of each substrate 210, 211 compared to the tooling surface, and the measured values are recorded in memory and used later to determine the gantry position to move to for final bond thickness correction. Accordingly, the computing system 120 causes the robotic placement head 220 to remain in a position where the first substrate 210 and the second substrate 211 are in close proximity, and the automated process of the optical bonding machine is suspended, stopped, ceased, or temporarily suspended or stopped. In response to the stoppage of the automated process, the computing system 120 may prompt an operator to take controls of the controller 110 to control the movement of the robotic placement head 220 to close the distance between the first substrate 210 and the second substrate 211 to effectuate a proper optical bond without formation of air pockets.

Figure 4:
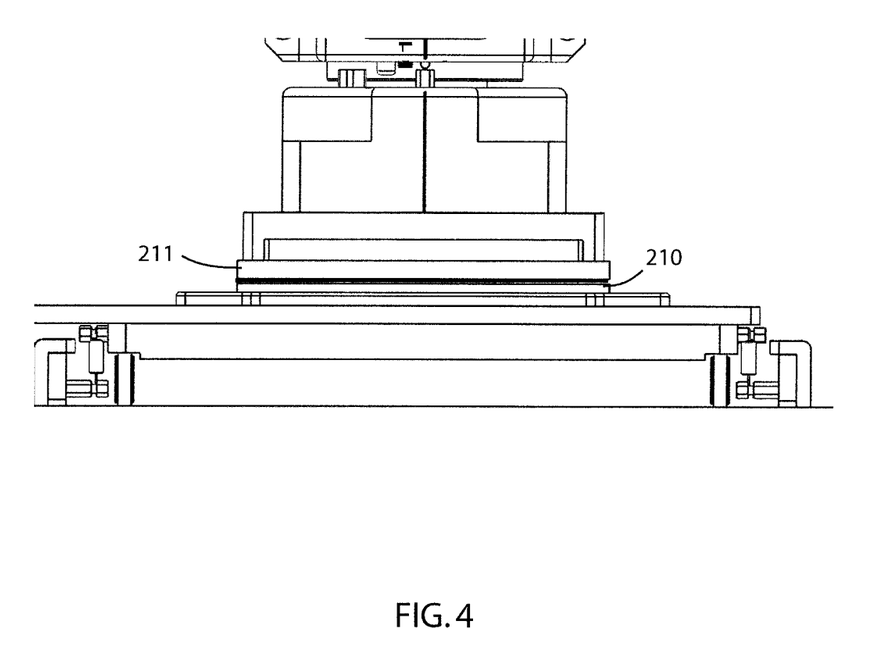
FIG. 4 depicts the substrates in an optically bonded position, in accordance with embodiments of the present invention.

Embodiments of the computing system 120 may include a control signal recording module 132. Embodiments of the control signal recording module 132 may include one or more components of hardware and/or software program code for recording, storing, tracking, monitoring, learning, etc. operator feedback control signals received from the controller 110 being operated by an operator to contact the first substrate 210 and the second substrate 211. For instance, the controller 110 may be coupled to the computing system 120 as shown in FIG. 1, and as the operator operates the controller 110, precise control signals are being sent from the controller 110 to the computing system 120 to effectuate the movement of the robotic placement head 220. Embodiments of the control signal recording module 132 may record, track, store, monitor, etc., those control signals sent from the controller 110. The control signals may be stored in the data repository 125 of the computing system 120, or may be transmitted to a remote storage device over network 107. Furthermore, the control signals being recorded by the control signal recording module 132 may include a plurality of factors from the recorded operator feedback control signals. The plurality of factors include steps, characteristics, movements, timing, and the like, which lead to the second substrate 211 to be optically bonded to the first substrate 210, as shown in FIG. 4. In other words, the factors may help determine a bond sequence of various commands that cause the robotic placement head 220 to lower the second substrate 211 onto the first substrate 210 and achieve a proper optical bond. The plurality of factors may include a time between moves, a speed of descent, a movement along an X axis, a movement along a Y axis, a movement along a Z axis, a tilt, a rotation, and the like, which may be helpful in determining the exact bond sequence to arrive at the optical bond position.

As the operator controls the robotic placement head 220 to effectuate an optical bond, the camera 111 may be capturing a real-time feed of the adhesive fill reaction, from underneath the transparent datum 225. The camera 111 may transmit the real-time feed to the computing system 120, which may then transmit the feed signal to the display 112. The operator may receive live feedback by viewing the display 112 to ensure a proper wavefront progression of the adhesive during contact and eventual bonding. The operator may input commands to the controller 110 based on the video feed displayed by the display 112, wherein the control signals sent from the controller 110 to the computing system 120 are being recorded by the control signal recording module 132.

Referring back to FIG. 1, embodiments of the computing system 120 may include an analytics module 133. Embodiments of the analytics module 133 may include one or more components of hardware and/or software program code for analyzing the operator feedback control signals to determine a bonding sequence for automatically optically bonding the first substrate 210 and the second substrate 211. For instance, embodiments of the analytics module 133 may analyze the plurality of factors from the recorded operator feedback control signals to create a sequential order for automatically controllably contacting the first substrate and the second substrate, based on the plurality of factors. The bonding sequence for automatically bonding the first substrate 210 and the second substrate 211 may include one or more commands for programming a movement of the robotic placement head 220 to optically bond the substrates 210, 211. The automatic bonding sequence may essentially be the exact moves/command signals that the operator input into the controller 110, except that the computing system 120 may provide the signals/instructions directly and automatically to the robotic placement head 220, without operator involvement. Thus, by analyzing and determining an automatic bond sequence based on an initial or single run-though of the operator controlling the controller 110, subsequent applications for complete optical bonding may be done entirely automatic (i.e. no stopping automatic process and waiting for operator to use controller 110. Embodiments of the bonding sequence may be used to contact a new first substrate of the same size as the first substrate 210 and a new second substrate of the same size as the second substrate 211, in a subsequent optical bonding operation, instead of the operator operating the controller 110. Moreover, embodiments of the analytics module 133 may derive a sequential order from the recorded signals, and may populate a database or programming directory that the computing system 120 accesses for providing commands to the robotic placement head 220, so that the subsequent optical bonding steps are automatically performed.

Furthermore, the plurality of factors stored in the database, such as data repository 125, may be further manipulated through a graphical user interface (e.g. a "bond manager tab") of the computing system 120, displayed on display 112. For example, an operator may interact with the graphical user interface to optimize the bond routine/sequence in a more refined manner making changes to any given factor; changes may be minute changes to refine the process. The first pass 'teach mode" (i.e. operator controlling controller 112) attempts to achieve a close to perfect bonding program/sequence. Then, a line-by-line editing of the bond step variables, such as speed, distance, dwell time, etc., may be performed using the graphical user interface to optimize the bond sequence for subsequent applications. As an example, the plurality of factors may be delineated in the GUI "bond manager tab" so each discrete value can be manipulated by keystroke entry, to optimize the bond sequence.

In an exemplary embodiment, an end user may utilize machine 200 having computing system 120 to perform repeatable, automatic optical bonding processes for various size substrates because an optimal bonding sequence may be learned by the computing system 120 in the field. An initial use for the machine 200 may involve optical bonding of covers/displays of smartphones. The machine 200 may ship to the end user, and an operator in the field may take the controls of the controller 110 to optical bond the cover/display of the smartphone using the real-time feedback on the display 112, courtesy of the camera 111 disposed in the interior 215 of the machine 200. Then, after the exact desired bonding sequence is learned by the computing system 120, subsequent runs may be completely automated. If the same end user desires to use machine 200 for optically bonding a cover/display for a tablet, which is a larger substrate area (and potentially a different adhesive, etc.), the end user need not contact the manufacturer and have the machine 200 entirely reprogrammed, but may indicate via a GUI of the software to initiate a learning process or tool, which will perform the steps described above, allowing an operator to use the controller 110 to manually optically bond the newly sized substrates using the feedback from the display 112. After the exact desired bonding sequence is learned by the computing system 120, subsequent runs may be completely automated.

With continued reference to FIG. 1, embodiments of the computing system 120 may include an inspection module 134. Embodiments of the inspection module 134 may include one or more components of hardware and/or software program code for inspecting the bonded substrates 210, 211 for a presence of air bubbles, foreign objects or debris, prior to resuming the automated process, or prior to initiating a curing step, wherein the inspecting includes examining a video or image of the bonded substrates 210, 211 captured by a camera 111 positioned beneath the first substrate 210. If air pockets are detected, then the inspection module 134 may cancel the curing step, and request new substrates and the process to start over. If no air pockets are detected, then the inspection module 134 may transmit a confirmation signal to the computing system 120, or may simply not send a cancel signal. The curing step involves actuating, by the processor of the computing system 120, a UV source 235 to move into a position beneath the bonded substrates 210, 211, which may cure the adhesive bonding the substrate 210, 211. Embodiments of the UV source 235 may an array of UV emitting lamps/lights, LED lamps/lights, mercury halide, or other UV emitting devices. Various UV sources 235 may be selected based on different wavelengths output by the UV device, which may be ideal for a particular adhesive used for the a particular project.

Embodiments of the computing system 120 may be equipped with a memory device 142 which may store the machine data and/or sequence data, and a processor 141 for implementing the tasks associated with the automatic bonding sequence learning system 100. Furthermore, various tasks and specific functions of the modules of the computing system 120 may be performed by additional modules, or may be combined into other module(s) to reduce the number of modules.

Figure 5:
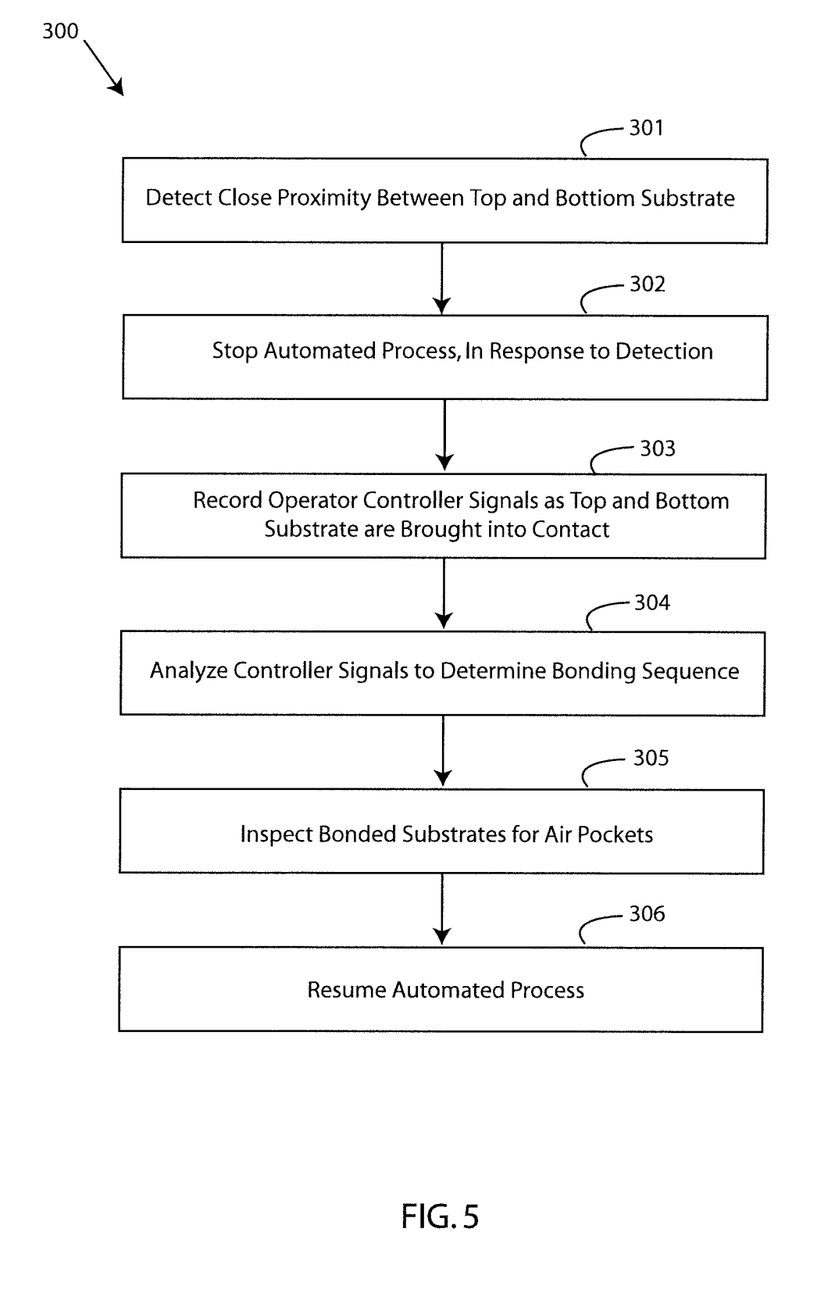
FIG. 5 depicts a flow chart of a method for customizing an automated bonding sequence, in accordance with embodiments of the present invention.

Referring now to FIG. 5, which depicts a flow chart of a method 300 for customizing an automated bonding sequence, in accordance with embodiments of the present invention. One embodiment of a method 300 or algorithm that may be implemented for customizing an automated bonding sequence in accordance with the automatic bonding sequence learning system 100 described in FIG. 1 using one or more computer systems as defined generically in FIG. 7 below, and more specifically by the specific embodiments of FIG. 1.

Embodiments of the method 300 for customizing an automated bonding sequence may begin at step 301 wherein a close proximity between the first substrate 210 and the second substrate 211 is detected. In response to the detection of step 301, step 302 stops the automated process, and may prompt a user/operator to use a controller 110 to maneuver the robotic placement head 220 to optically bond the substrates 210, 211, in view of the real-time feedback provided by the camera 111 in the machine 200. Step 303 records the operator controller signals as the substrates 210, 211 are brought into contact. Step 304 analyzes the controller signals to determine an automatic bonding sequence, which may be used for subsequent applications/processes without operator intervention for maneuvering the robotic placement head 220. Step 305 inspects the bonded substrates 210, 211 for air pockets, prior to a curing step to cure the adhesive. Step 306 resumes the automated process, which may include actuating the UV source 235 to move (e.g. along a track within the machine 200) into a position below the bonded substrates and cure the adhesive while the robotic gripper continues to hold the upper substrate at the desired X, Y, Z and rotational position. The result is properly oriented and desired bond thickness product being cured before removal to the remaining automated steps. The curing may be done in the same interior region 215 of the machine 200 as the optical bonding because the datum 225, and the substrates are transparent.

Figure 6:
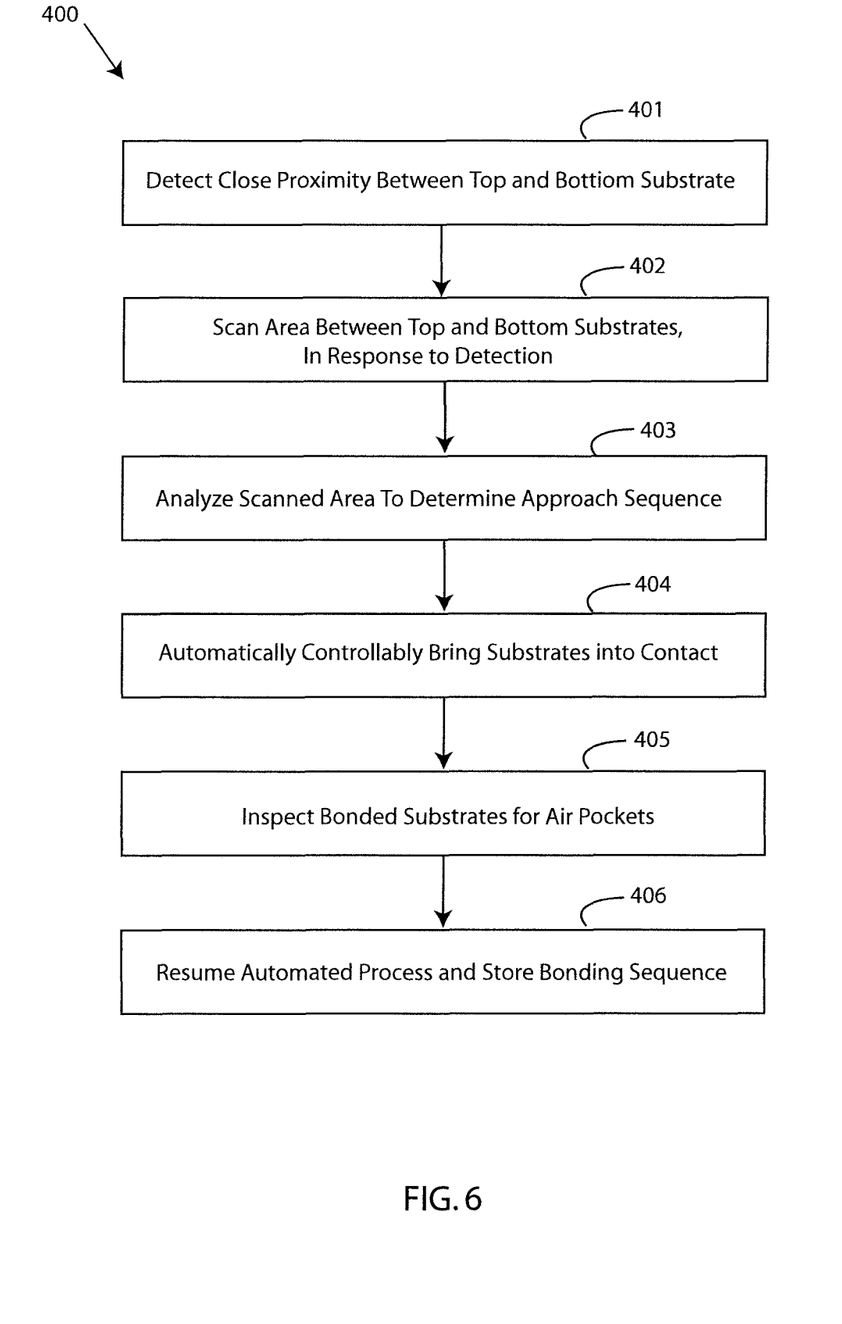
FIG. 6 depicts a flow chart of a method for automatically determining a bonding sequence, in accordance with embodiments of the present invention.
Figure 7:
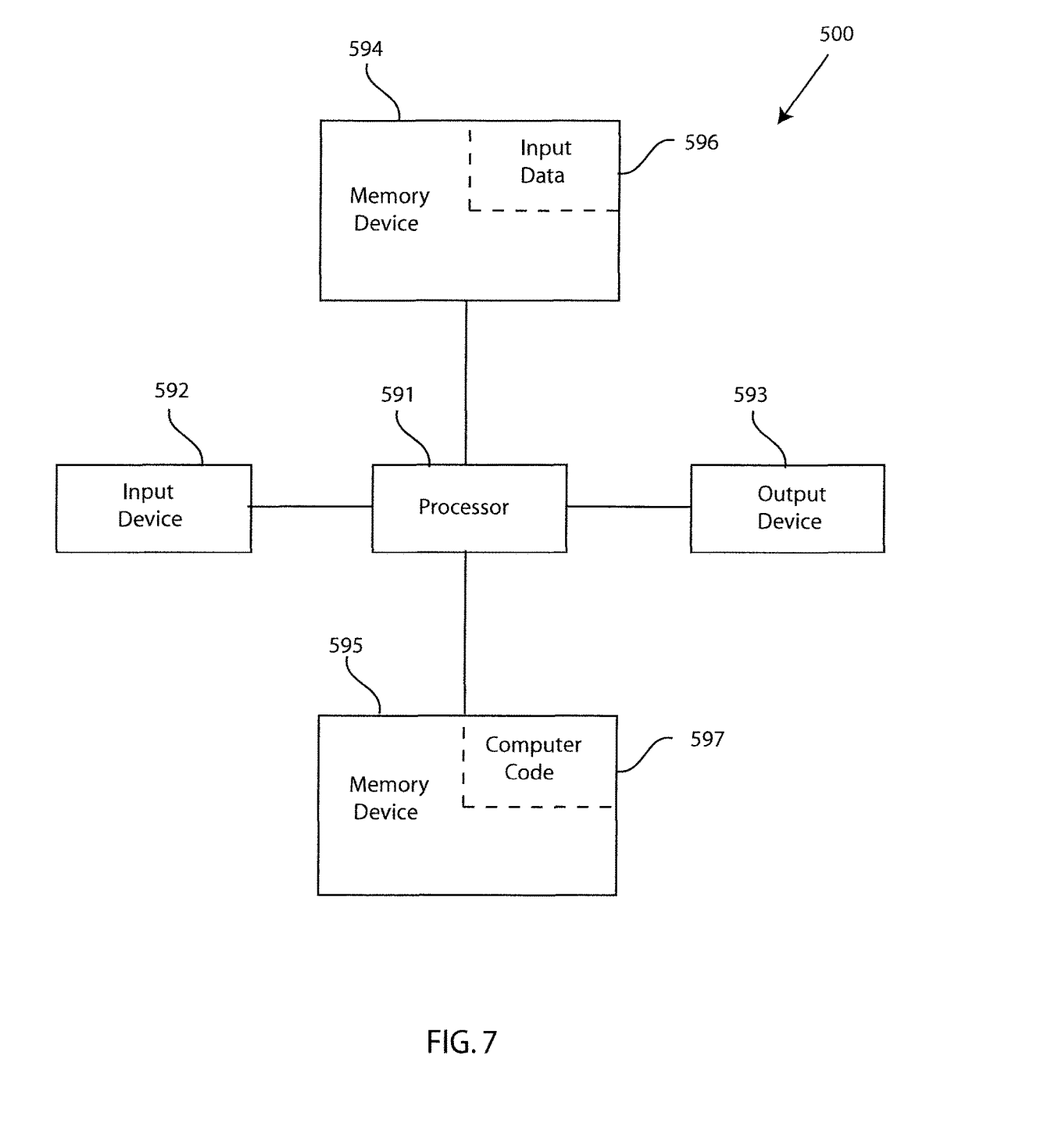
FIG. 7 depicts a block diagram of a computer system for the automatic bonding sequence learning system of FIG. 1, capable of implementing methods for customizing an automated bonding sequence of FIGS. 5-6, in accordance with embodiments of the present invention.

In an alternative embodiment, the computing system 120 automatically determines or suggests a bonding sequence, without operator involvement, or learning a sequence as input by an operator using a controller 110. FIG. 6 depicts a flow chart of a method 400 for automatically determining a bonding sequence, in accordance with embodiments of the present invention. Step 401 detects a close proximity between the first substrate 210 and the second substrate 211. In response the detection of step 401, step 402 scans an area (e.g. gap) between the substrates 210, 210. The scanning may be performed by a laser, a sensor, a camera, an ultrasound sensor, and the like, which may be positioned within the machine 200. Step 404 analyzes the data returned to the computing system 120. For instance, the scanning of the area may help determine how much the robotic placement head 220 has to move in each of the X, Y, Z axes, which may also take into account a fill height of the adhesive, and well as the chemical and physical properties of the adhesive (e.g. viscosity, etc.). Further data may retrieved by one or more sensors, such as a weight of the substrate(s), a thickness of the substrate(s), a fill height of the adhesive, and the like. The computing system 120 may also analyze the display 112 for rate of progression of the wavefront of the adhesive's capillary effect when the substrates 210, 211 are being bonded, to aid in the determining of the automatic bonding sequence. The analysis of the scanned data, the image/video of the adhesive flow, properties of the adhesive, a fill height of the adhesive, a thickness of the substrate(s), a weight of the substrate(s), and the like, may be used to determine a bond sequence that will lead to a proper optical bond. Step 405 inspects the bonded substrates 210, 211 for air pockets, prior to a curing step to cure the adhesive. Step 406 resumes the automated process and stores the bonding sequence, which may include actuating the UV source 235 to move (e.g. along a track within the machine 200) into a position below the bonded substrates and cure the adhesive. The curing may be done in the same interior region 215 of the machine 200 as the optical bonding because the datum 225, and the substrates are transparent. Furthermore, method 400 may be repeated FIG. 7 depicts a block diagram of a computer system for the automatic bonding sequence learning system of FIG. 1, capable of implementing methods for customizing an automated bonding sequence of FIGS. 5-6, in accordance with embodiments of the present invention. The computer system 500 may generally comprise a processor 591, an input device 592 coupled to the processor 591, an output device 593 coupled to the processor 591, and memory devices 594 and 595 each coupled to the processor 591. The input device 592, output device 593 and memory devices 594, 595 may each be coupled to the processor 591 via a bus. Processor 591 may perform computations and control the functions of computer 500, including executing instructions included in the computer code 597 for the tools and programs capable of implementing a method for customizing an automated bonding sequence, in the manner prescribed by the embodiments of FIGS. 5-6 using the automatic bonding sequence learning system of FIG. 1, wherein the instructions of the computer code 597 may be executed by processor 591 via memory device 595. The computer code 597 may include software or program instructions that may implement one or more algorithms for implementing the methods of customizing an automated bonding sequence, as described in detail above. The processor 591 executes the computer code 597. Processor 591 may include a single processing unit, or may be distributed across one or more processing units in one or more locations (e.g., on a client and server).

The memory device 594 may include input data 596. The input data 596 includes any inputs required by the computer code 597. The output device 593 displays output from the computer code 597. Either or both memory devices 594 and 595 may be used as a computer usable storage medium (or program storage device) having a computer readable program embodied therein and/or having other data stored therein, wherein the computer readable program comprises the computer code 597. Generally, a computer program product (or, alternatively, an article of manufacture) of the computer system 500 may comprise said computer usable storage medium (or said program storage device).

Memory devices 594, 595 include any known computer readable storage medium, including those described in detail below. In one embodiment, cache memory elements of memory devices 594, 595 may provide temporary storage of at least some program code (e.g., computer code 597) in order to reduce the number of times code must be retrieved from bulk storage while instructions of the computer code 597 are executed. Moreover, similar to processor 591, memory devices 594, 595 may reside at a single physical location, including one or more types of data storage, or be distributed across a plurality of physical systems in various forms. Further, memory devices 594, 595 can include data distributed across, for example, a local area network (LAN) or a wide area network (WAN). Further, memory devices 594, 595 may include an operating system (not shown) and may include other systems not shown in FIG. 7.

In some embodiments, the computer system 500 may further be coupled to an Input/output (I/O) interface and a computer data storage unit. An I/O interface may include any system for exchanging information to or from an input device 592 or output device 593. The input device 592 may be, inter alia, a keyboard, a mouse, etc. or in some embodiments the sensors 110. The output device 593 may be, inter alia, a printer, a plotter, a display device (such as a computer screen), a magnetic tape, a removable hard disk, a floppy disk, etc. The memory devices 594 and 595 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus may provide a communication link between each of the components in computer 500, and may include any type of transmission link, including electrical, optical, wireless, etc.

An I/O interface may allow computer system 500 to store information (e.g., data or program instructions such as program code 597) on and retrieve the information from computer data storage unit (not shown). Computer data storage unit includes a known computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk). In other embodiments, the data storage unit may include a knowledge base or data repository 125 as shown in FIG. 1.

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider that offers to deploy or integrate computing infrastructure with respect to an automated bonding sequence systems and methods. Thus, an embodiment of the present invention discloses a process for supporting computer infrastructure, where the process includes providing at least one support service for at least one of integrating, hosting, maintaining and deploying computer-readable code (e.g., program code 597) in a computer system (e.g., computer 500) including one or more processor(s) 591, wherein the processor(s) carry out instructions contained in the computer code 597 causing the computer system to customize an automated bonding sequence. Another embodiment discloses a process for supporting computer infrastructure, where the process includes integrating computer-readable program code into a computer system including a processor.

The step of integrating includes storing the program code in a computer-readable storage device of the computer system through use of the processor. The program code, upon being executed by the processor, implements a method of customizing an automated bonding sequence. Thus, the present invention discloses a process for supporting, deploying and/or integrating computer infrastructure, integrating, hosting, maintaining, and deploying computer-readable code into the computer system 500, wherein the code in combination with the computer system 500 is capable of performing a method for customizing an automated bonding sequence.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for customizing an automated bonding sequence, the method comprising:
    detecting, by a processor of a computing system, that a first substrate is in close proximity with a second substrate, during an optical bonding operation, wherein at least the first substrate includes an amount of adhesive for optically bonding to the second substrate;
    stopping, by the processor, an automated process of optically bonding of the optical bonding operation, in response to the detecting;
    recording, by the processor, operator feedback control signals, the operator feedback control signals being received from a controller being operated by an operator to contact the first substrate and the second substrate;
    analyzing, by the processor, the operator feedback control signals to determine a bonding sequence for automatically optically bonding the first substrate and the second substrate; and
    resuming, by the processor, the automated process of the optical bonding operation.

2. The method of claim 1, wherein the bonding sequence is used to contact a new first substrate of the same size as the first substrate and a new second substrate of the same size as the second substrate, in a subsequent optical bonding operation, instead of the operator operating the controller.

3. The method of claim 1, wherein the analyzing the operator feedback control signals to determine the bonding sequence comprises:
    analyzing, by the processor, a plurality of factors from the recorded operator feedback control signals; and
    creating, by the processor, a sequential order for automatically controllably contacting the first substrate and the second substrate, based on the plurality of factors.

4. The method of claim 3, wherein the plurality of factors include a distance moved along a X axis, a distance moved along a Y axis, a distance moved along a Z axis, a rotation about the yaw axis, a wait time between moves, a speed, a rate of progression causing of a capillary effect of the adhesive between the first substrate and the second substrate.

5. The method of claim 4, wherein the resuming the automated process including, actuating, by the processor, an array of UV lights, moved into position to cure the optical bonding between the first substrate and the second substrate.

6. The method of claim 1, further comprising:
inspecting, by the processor, the bonded substrates for a presence of defects prior to the resuming, wherein the inspecting includes examining a video or image of the bonded substrates captured by a camera positioned beneath the first substrate.

7. The method of claim 1, wherein at least one of the first substrate and the second substrate are transparent.

8. A computer system, comprising:
a processor;
a memory device coupled to the processor; and
a computer readable storage device coupled to the processor, wherein the storage device contains program code executable by the processor via the memory device to implement a method customizing an automated bonding sequence, the method comprising:
detecting, by a processor of a computing system, that a first substrate is in close proximity with a second substrate, during an optical bonding operation, wherein at least the first substrate includes an amount of adhesive for optically bonding to the second substrate;
stopping, by the processor, an automated process of optically bonding of the optical bonding operation, in response to the detecting;
recording, by the processor, operator feedback control signals, the operator feedback control signals being received from a controller being operated by an operator to contact the first substrate and the second substrate;
analyzing, by the processor, the operator feedback control signals to determine a bonding sequence for automatically optically bonding the first substrate and the second substrate; and
resuming, by the processor, the automated process of the optical bonding operation.

9. The computer system of claim 8, wherein the bonding sequence is used to contact a new first substrate of the same size as the first substrate and a new second substrate of the same size as the second substrate, in a subsequent optical bonding operation, instead of the operator operating the controller.

10. The computer system of claim 8, wherein the analyzing the operator feedback control signals to determine the bonding sequence comprises:
analyzing, by the processor, a plurality of factors from the recorded operator feedback control signals; and
creating, by the processor, a sequential order for automatically controllably contacting the first substrate and the second substrate, based on the plurality of factors.

11. The computer system of claim 10, wherein the plurality of factors include a distance moved along a X axis, a distance moved along a Y axis, a distance moved along a Z axis, rotation about the yaw axis, a wait time between moves, a speed, a rate of progression of each axis causing a capillary effect of the adhesive between the first substrate and the second substrate.

12. The computer system of claim 8, further comprising:
inspecting, by the processor, the bonded substrates for a presence of defects, prior to the resuming, wherein the inspecting includes examining a video or image of the bonded substrates captured by a camera positioned beneath the first substrate.

13. The computer system of claim 12, wherein the resuming the automated process including, actuating, by the processor, an array of UV lights, moved into position to cure the optical bonding between the first substrate and the second substrate.

14. The computer system of claim 8, wherein at least one of the first substrate and the second substrate are transparent.

15. A computer program product, comprising a computer readable hardware storage device storing a computer readable program code, the computer readable program code comprising an algorithm that when executed by a computer processor of a computing system implements a method customizing an automated bonding sequence, the method comprising:
detecting, by a processor of a computing system, that a first substrate is in close proximity with a second substrate, during an optical bonding operation, wherein at least the first substrate includes an amount of adhesive for optically bonding to the second substrate;
stopping, by the processor, an automated process of optically bonding of the optical bonding operation, in response to the detecting;
recording, by the processor, operator feedback control signals, the operator feedback control signals being received from a controller being operated by an operator to contact the first substrate and the second substrate;
analyzing, by the processor, the operator feedback control signals to determine a bonding sequence for automatically optically bonding the first substrate and the second substrate; and
resuming, by the processor, the automated process of the optical bonding operation.

16. The computer program product of claim 15, wherein the bonding sequence is used to contact a new first substrate of the same size as the first substrate and a new second substrate of the same size as the second substrate, in a subsequent optical bonding operation, instead of the operator operating the controller.

17. The computer program product of claim 15, wherein the analyzing the operator feedback control signals to determine the bonding sequence comprises:
analyzing, by the processor, a plurality of factors from the recorded operator feedback control signals; and
creating, by the processor, a sequential order for automatically controllably contacting the first substrate and the second substrate, based on the plurality of factors.

18. The computer program product of claim 17, wherein the plurality of factors include a distance moved along a X axis, a distance moved along a Y axis, a distance moved along a Z axis, a rotation about yaw axis, a wait time between moves, a speed, a rate of progression of the axes causing a capillary effect of the adhesive between the first substrate and the second substrate.

19. The computer program product of claim 15, wherein the analyzing of the operator feedback control signals to determine the bonding sequence produces a delineation of the plurality of values that are manipulated for further bond routine optimization.

20. The computer program product of claim 15, further comprising:
inspecting, by the processor, the bonded substrates for a presence of defects, prior to the resuming, wherein the inspecting includes examining a video or image of the bonded substrates captured by a camera positioned beneath the first substrate.

\* \* \* \* \*